United States Patent
Hao et al.

(10) Patent No.: US 10,874,367 B2
(45) Date of Patent: Dec. 29, 2020

(54) ANGIOGRAPHY (71) Applicant: BEIJING NEUSOFT MEDICAL EQUIPMENT CO., LTD., Beijing (CN)

(72) Inventors: Huaming Hao, Shenyang (CN); Jianxun Liu, Shenyang (CN)

(73) Assignee: BEIJING NEUSOFT MEDICAL EQUIPMENT CO., LTD., Beijing (CN)

(*) Notice: Subject to any disclaimer, the term of this patent is extended or adjusted under 35 U.S.C. 154(b) by 92 days.

(21) Appl. No.: 16/424,300

(22) Filed: May 28, 2019

(65) Prior Publication Data
US 2019/0365340 A1 Dec. 5, 2019

(30) Foreign Application Priority Data
May 29, 2018 (CN) .......................... 2018 1 0531258

(51) Int. Cl.
*G06K 9/00* (2006.01)
*A61B 6/00* (2006.01)
*G06T 7/254* (2017.01)
*G06T 5/50* (2006.01)
*G06T 5/00* (2006.01)

(52) U.S. Cl.
CPC .............. *A61B 6/504* (2013.01); *A61B 6/481* (2013.01); *G06T 5/50* (2013.01); *G06T 7/254* (2017.01); *A61B 6/5229* (2013.01); *G06T 5/002* (2013.01); *G06T 2207/10116* (2013.01); *G06T 2207/20224* (2013.01); *G06T 2207/30101* (2013.01)

(58) Field of Classification Search
CPC ....... A61B 6/504; A61B 6/481; A61B 6/5229; A61B 6/42; A61B 6/54; G06T 7/254; G06T 5/50; G06T 5/002; G06T 2207/10116; G06T 2207/20224; G06T 2207/30101
USPC .......................................................... 382/130
See application file for complete search history.

(56) References Cited

U.S. PATENT DOCUMENTS

| | | | |
|---|---|---|---|
| 9,189,848 B2* | 11/2015 | Sakaguchi | G06T 7/0014 |
| 9,265,474 B2* | 2/2016 | Machida | A61B 6/504 |
| 2003/0073903 A1* | 4/2003 | Sato | G01S 15/8988 |
| | | | 600/437 |
| 2003/0215055 A1* | 11/2003 | Ozawa | A61B 6/504 |
| | | | 378/62 |
| 2007/0104317 A1* | 5/2007 | Ohishi | A61B 6/481 |
| | | | 378/98.12 |

(Continued)

*Primary Examiner* — Van D Huynh
(74) *Attorney, Agent, or Firm* — Fish & Richardson P.C.

(57) ABSTRACT

Methods, systems, devices and storage mediums for angiography are provided. In one aspect, a method includes: obtaining a first contrast image sequence collected by a X-ray detector of a DSA system at a first position; obtaining a flow path of a contrast medium by analyzing the first contrast image sequence; when the contrast medium is about to flow out of a collection area of the X-ray detector according to the flow path, controlling the X-ray detector to move to a second position, so that the contrast medium remains within the collection area; when the X-ray detector is located at the second position, obtaining a virtual mask image based on a last frame of the first contrast image sequence and a first frame of a second contrast image sequence collected by the X-ray detector at the second position; and generating a DSA image sequence by using the virtual mask image.

20 Claims, 6 Drawing Sheets (56) References Cited

U.S. PATENT DOCUMENTS

| | | | |
|---|---|---|---|
| 2011/0235885 A1* | 9/2011 | Rauch | A61B 6/504 382/131 |
| 2016/0029987 A1* | 2/2016 | Langan | A61B 6/025 378/8 |
| 2018/0064336 A1* | 3/2018 | Kano | G06T 5/50 |
| 2019/0192091 A1* | 6/2019 | Lee | A61B 6/463 |

* cited by examiner

Second contrast image    Virtual mask image    DSA image

ANGIOGRAPHY

CROSS REFERENCE TO RELATED APPLICATIONS

This application claims priority to Chinese Patent Application No. 201810531258.2 filed on May 29, 2018, the entire content of which is incorporated herein by reference.

BACKGROUND

A Digital Subtraction Angiography (DSA) system is an X-ray imaging system combining a conventional angiography technology with an electronic computer image processing technology. Angiography may be performed by using the DSA system based on the following principle. Images of a detected region before and after the injection of a contrast medium into a blood vessel are collected by a fixedly-placed X-ray detector. An image collected before the injection of the contrast medium is referred to as a mask image, and an image collected after the injection of the contrast medium is referred to as a contrast image. After subtracting the mask image from the contrast image by a computer, a subtracted image including only information of the blood vessel, that is, a DSA image, may be obtained. The DSA image may provide a clear image basis for subsequent diagnosis and treatment.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

SUMMARY

The present disclosure provides methods, devices, systems and apparatus for angiography applied in DSA systems, which can effectively improve the angiographic efficiency.

The present disclosure provides methods, devices, systems and apparatus for angiography applied in DSA systems, which can effectively improve the angiographic efficiency.

One aspect of the present disclosure features an angiography method for a Digital Subtraction Angiography (DSA) system including an X-ray detector. The method includes: obtaining a first contrast image sequence including a plurality of frames of contrast images collected by the X-ray detector at a first position after a contrast medium flows into a collection area of the X-ray detector; generating a flow path of the contrast medium by analyzing the first contrast image sequence; in response to determining that the contrast medium is about to flow out of the collection area of the X-ray detector according to the flow path, controlling the X-ray detector to move to a second position, so that the contrast medium remains within the collection area of the X-ray detector; and when the X-ray detector is located at the second position, generating a virtual mask image based on a mask image collected when the X-ray detector is located at the first position and before the contrast medium flows into the collection area, a last frame of contrast image collected when the X-ray detector is located at the first position and a first frame of contrast image collected when the X-ray detector is located at the second position.

In some implementations, generating the flow path of the contrast medium includes: obtaining a plurality of frames of pseudo subtracted images including information of the contrast medium by subtracting every two adjacent frames of the plurality of frames of contrast images in the first contrast image sequence; and generating the flow path of the contrast medium by splicing the information of the contrast medium in the plurality of frames of pseudo subtracted images.

Obtaining the plurality of frames of pseudo subtracted images can include: for every two adjacent frames of the plurality of frames of contrast images, performing respective convolution smoothing for each of the two adjacent frames of the plurality of frames of contrast images; generating an initial subtracted image by performing subtraction for the two adjacent convolution smoothed frames of contrast images; and determining a pixel in the initial subtracted image having a pixel value lower than a preset pixel threshold to be a pixel of a pseudo subtracted image for the two adjacent frames of the plurality of frames of contrast images.

In some implementations, the collection area of the X-ray detector includes a safety zone and a transition zone. Controlling the X-ray detector to move to the second position can include: in response to determining that the contrast medium is about to flow from the safety zone into the transition zone according to the flow path, controlling the X-ray detector to move to the second position so that the contrast medium re-enters the safety zone of the collection area of the X-ray detector. In some cases, a moving distance of the X-ray detector from the first position to the second position is determined based on a flow distance of the contrast medium in at least two frames of contrast images collected by the X-ray detector at the first position or at a present position, such that the contrast medium is kept within the collection area of the X-ray detector.

In some cases, controlling the X-ray detector to move to the second position includes: calculating a fitting curve of the contrast medium according to the flow path of the contrast medium; determining a moving direction of the X-ray detector according to an endpoint of the fitting curve and a tangent of the fitting curve; and controlling the X-ray detector to move to the second position along the moving direction.

In some implementations, obtaining the virtual mask image when the X-ray detector is located at the second position includes: taking the last frame of contrast image collected when the X-ray detector is located at the first position as a first reference contrast image; taking the first frame of contrast image collected when the X-ray detector is located at the second position as a second reference contrast image; generating a difference image between the second reference contrast image and the first reference contrast image; and obtaining the virtual mask image by adding the difference image and the mask image.

Generating the difference image between the second reference contrast image and the first reference contrast image can include: determining offset values that reflect the first reference contrast image relative to the second reference contrast image; moving the first reference contrast image according to the offset values; and generating the difference image by subtracting the second reference contrast image from the moved first reference contrast image. In some cases, determining the offset values includes: comparing pixel values of the first reference contrast image with pixel values of the second reference contrast image along the moving direction in which the X-ray detector moves from the first position to the second position; and determining the offset values in a two-dimensional direction according to a result of the comparison. In some cases, determining the offset values includes: generating a first smoothed contrast image and a second smoothed contrast image by performing convolution smoothing for the first reference contrast image and the second reference contrast image, respectively; comparing pixel values of the first smoothed contrast image with pixel values of the second smoothed contrast image along the moving direction; determining edges of the first smoothed contrast image in the second smoothed contrast image according to a result of the comparison; and determining the offset values in a two-dimensional direction according to distance between the edges of the first smoothed contrast image in the second smoothed contrast image and edges of the second smoothed contrast image. In some cases, obtaining the virtual mask image by adding the difference image and the mask image includes: moving the mask image according to the offset values; and obtaining the virtual mask image by adding the moved mask image and the difference image.

The method can further include obtaining a DSA image sequence by obtaining a second contrast image sequence including a plurality of frames of second contrast images collected by the X-ray detector at the second position, performing convolution smoothing for the virtual mask image, and for each frame of second contrast image in the second contrast image sequence: performing convolution smoothing for the frame of second contrast image; and generating a respective DSA image by subtracting the convolution smoothed virtual mask image from the convolution smoothed frame of second contrast image, where the DSA image sequence includes the respective DSA images for the frames of second contrast images in the second contrast image sequence. Obtaining the DSA image sequence can further include: generating respective first DSA images by using the mask image and the frames of contrast images in the first contrast image sequence, where the DSA image sequence includes the respective first DSA images for the frames of contrast images in the first contrast image sequence.

Another aspect of the present disclosure features a Digital Subtraction Angiography (DSA) system including: a DSA main device including an examination bed, a fixed gantry, a rotatable mechanical arm arranged on the fixed gantry, and an X-ray emitter and an X-ray detector which are mounted on two ends of the mechanical arm, the X-ray detector being configured to collect contrast images and a mask image, and an image processing device configured to: obtain a first contrast image sequence including a plurality of frames of contrast images collected by the X-ray detector at a first position after a contrast medium flows into a collection area of the X-ray detector; generate a flow path of the contrast medium by analyzing the first contrast image sequence; in response to determining that the contrast medium is about to flow out of the collection area of the X-ray detector according to the flow path, control the X-ray detector to move to a second position, so that the contrast medium remains within the collection area of the X-ray detector; when the X-ray detector is located at the second position, obtain a virtual mask image based on a mask image collected when the X-ray detector is located at the first position, a last frame of contrast image of the first contrast image sequence collected when the X-ray detector is located at the first position and a first frame of contrast image of a second contrast image sequence collected when the X-ray detector is located at the second position; and generate a DSA image sequence by using the virtual mask image and the second contrast image sequence.

The image processing device can be configured to generate the flow path of the contrast medium by obtaining a plurality of frames of pseudo subtracted images including information of the contrast medium by subtracting every two adjacent frames of the plurality of frames of contrast images in the first contrast image sequence and generating the flow path of the contrast medium by splicing the information of the contrast medium in the plurality of frames of pseudo subtracted images.

In some implementations, the collection area of the X-ray detector includes a safety zone and a transition zone, and the image processing device is configured to control the X-ray detector to move to the second position by controlling the X-ray detector to move to the second position in response to determining that the contrast medium is about to flow from the safety zone into the transition zone according to the flow path so that the contrast medium re-enters the safety zone of the collection area of the X-ray detector.

The image processing device can be configured to obtain the virtual mask image by determining offset values that reflect the last frame of contrast image of the first contrast image sequence as a first reference contrast image relative to the first frame of contrast image of the second contrast image sequence as a second reference contrast image, moving the first reference contrast image according to the offset values, generating a difference image by subtracting the second reference contrast image from the moved first reference contrast image, moving the mask image according to the offset values, and adding the difference image and the moved mask image to obtain the virtual mask image.

The image processing device can be configured to generate the DSA image sequence by performing convolution smoothing for the virtual mask image and for each frame of second contrast image in the second contrast image sequence: performing convolution smoothing for the frame of second contrast image; and generating a respective DSA image by subtracting the convolution smoothed virtual mask image from the convolution smoothed frame of second contrast image, where the DSA image sequence includes the respective DSA images for the frames of second contrast images in the second contrast image sequence.

A further aspect of the present disclosure features an image processing device of a Digital Subtraction Angiography (DSA) system including an X-ray detector, the image processing device including: at least one processor; a memory configured to store machine readable instructions corresponding to a control logic for angiography; an external interface configured to connect the X-ray detector; and an internal bus through which the memory, the processor, and the external interface are connected. The processor is configured to read the machine readable instructions in the memory and execute the instructions to perform operations including: obtaining a first contrast image sequence including a plurality of frames of contrast images collected by the X-ray detector at a first position after a contrast medium flows into a collection area of the X-ray detector; generating a flow path of the contrast medium by analyzing the first contrast image sequence; in response to determining that the contrast medium is about to flow out of the collection area of the X-ray detector according to the flow path, controlling the X-ray detector to move to a second position, so that the contrast medium remains within the collection area of the X-ray detector; when the X-ray detector is located at the second position, obtaining a virtual mask image based on a mask image collected when the X-ray detector is located at the first position, a last frame of contrast image of the first contrast image sequence collected when the X-ray detector is located at the first position and a first frame of contrast image of a second contrast image sequence collected when the X-ray detector is located at the second position; and generating a DSA image sequence by using the virtual mask image and the second contrast image sequence.

Other embodiments of these aspects include corresponding computer systems, apparatus, and computer programs recorded on one or more computer storage devices, each configured to perform the actions of the methods. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

The details of one or more examples of the subject matter described in the present disclosure are set forth in the accompanying drawings and description below. Other features, aspects, and advantages of the subject matter will become apparent from the description, the drawings, and the claims. Features of the present disclosure are illustrated by way of example and not limited in the following figures, in which like numerals indicate like elements.

DETAILED DESCRIPTION

Examples will be described in detail here with the examples thereof shown in the drawings. Where the following descriptions involve the drawings, like numerals in different drawings refer to like or similar elements unless otherwise indicated. The embodiments described in the following examples do not represent all embodiments consistent with the present disclosure. Rather, they are merely examples of apparatuses and methods consistent with some aspects of the present disclosure as detailed in the appended claims.

Figure 1:
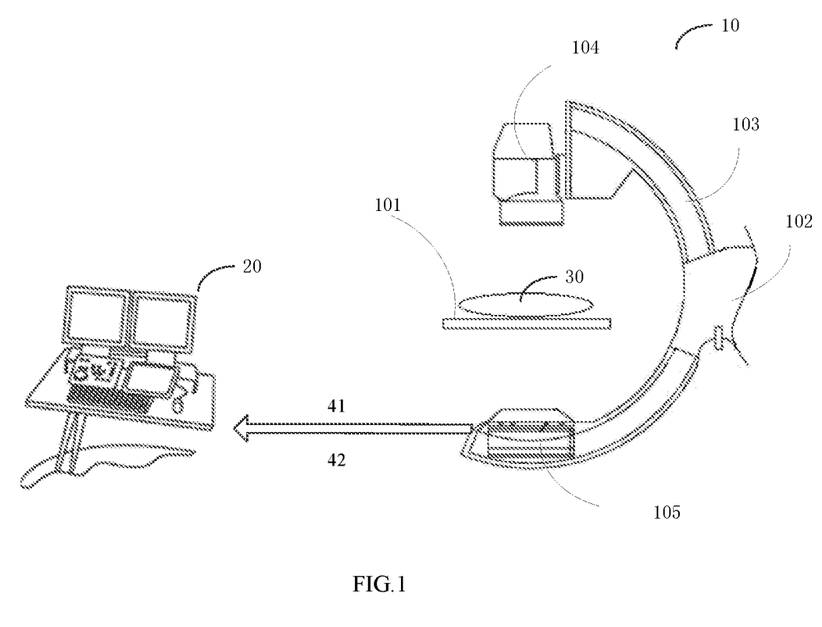
FIG. 1 is a schematic diagram illustrating a DSA system according to an example of the present disclosure.

The DSA technology is a technology in which a DSA image including information of a blood vessel is retained by performing digitalization processing for a contrast image to remove unnecessary information of tissues. The DSA image has the characteristics of a good image sharpness and a high resolution. The DSA image provides a real stereoscopic image for observation of vascular lesions, especially for vascular stenosis position measurement, diagnosis and interventional treatment. The DSA image also provides a necessary condition for various interventional treatments. FIG. 1 is a schematic diagram illustrating a DSA system using the DSA technology according to an example of the present disclosure.

As shown in FIG. 1, the DSA system includes: a DSA main device 10 and an image processing device 20. The DSA main device 10 may include: an examination bed 101, a fixed gantry 102, a rotatable mechanical arm 103 (such as a C-shaped arm as shown in FIG. 1) arranged on the fixed gantry 102, and an X-ray emitter 104 and an X-ray detector 105 which are mounted on both ends of the mechanical arm 103. The image processing device 20 is connected with the DSA main device 10 to obtain a contrast image 41 and a mask image 42 collected by the X-ray detector 105.

In another example of a DSA system, the main device 10 may transmit contrast image data and mask image data collected by the X-ray detector 105 to the image processing device 20, and the image processing device 20 may generate a corresponding contrast image and a corresponding mask image according to the data. A specific position of the image processing device for generating the contrast image and the mask image is not limited herein. A description will be made below with the contrast image and the mask image obtained in the main device 10 as an example.

During angiography, a subject 30 may lie on the examination bed 101. After the mechanical arm 103 moves to a target position, positions of the X-ray emitter 104 and the X-ray detector 105 are also relatively fixed. At this time, the X-ray emitter 104 is configured to emit X-rays, and correspondingly, the X-ray detector 105 is configured to detect X-rays attenuated by the subject 30, convert the X-rays into digital data, generate a digital image according to the data, and output the digital image to the image processing device 20. The X-ray detector 105 may collect a mask image of the subject before a contrast medium is injected into the subject 30, and may collect a contrast image of the subject after a particular dose of contrast medium is injected into the subject 30 by a contrast medium injector. A DSA image of the subject 30 may be obtained by subtracting the mask image from the contrast image.

In an example, the positions of the X-ray emitter 104 and the X-ray detector 105 are fixed. After the contrast medium is injected into the subject, the contrast medium flows within a blood vessel of the subject. When the contrast medium flows out of a collection area of the X-ray detector 105, the positions of the X-ray detector 105 and the X-ray emitter 104 need to be manually adjusted, and a DSA image is regenerated. Therefore, the entire adjustment process is cumbersome, resulting in a low angiographic efficiency. Based on this, in an example of the present disclosure, the X-ray detector may be controlled to move before it is determined that the contrast medium is about to flow out of a collection area of the X-ray detector by analyzing a flow path of the contrast medium. In this way, it is ensured that a contrast image reflecting information of the contrast medium is always located within the collection area of the X-ray detector by automatically controlling the X-ray detector to move, and a virtual mask image corresponding to a moved position of the X-ray detector may be obtained by calculation, thereby effectively improving the angiographic efficiency. In the present disclosure, the relative positions of the X-ray detector and the X-ray emitter are fixed, and controlling the movement of the X-ray detector may be implemented by controlling the movement of the mechanical arm where the X-ray detector is mounted, and at the same time, the X-ray emitter also moves with the X-ray detector.

An example of an angiography method of the present disclosure will be described below in detail in combination with the DSA system as shown in FIG. 1.

Figure 2A:
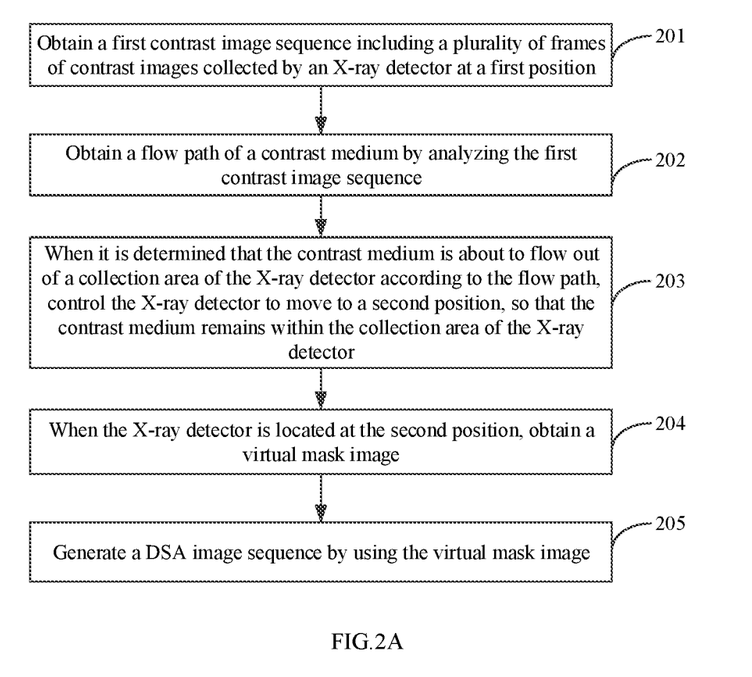
FIG. 2A is a flowchart illustrating a process of an angiography method according to an example of the present disclosure.

FIG. 2A is a flowchart illustrating a process of an angiography method according to an example of the present disclosure, and the example may include the following steps.

At step 201, a first contrast image sequence including a plurality of frames of contrast images collected by an X-ray detector at a first position is obtained.

In an example, a contrast medium may reach a detected region of a subject in a period of time after being injected into the subject. An image collected by the X-ray detector before the contrast medium is injected or before the contrast medium reaches the detected region is referred to a mask image, and an image collected by the X-ray detector after the contrast medium reaches the detected region is referred to a contrast image. Since the contrast medium within the subject may gradually decrease and disappear after a period of time, the X-ray detector needs to complete collection of the contrast images before the contrast medium disappears.

At this step, the X-ray detector is firstly set at the first position to perform angiography for the subject. The X-ray detector may collect the mask image at the first position. During the flow of contrast medium, the X-ray detector may collect the first contrast image sequence according to a preset time interval, where the first contrast image sequence includes a plurality of frames of contrast images.

Figure 2B:
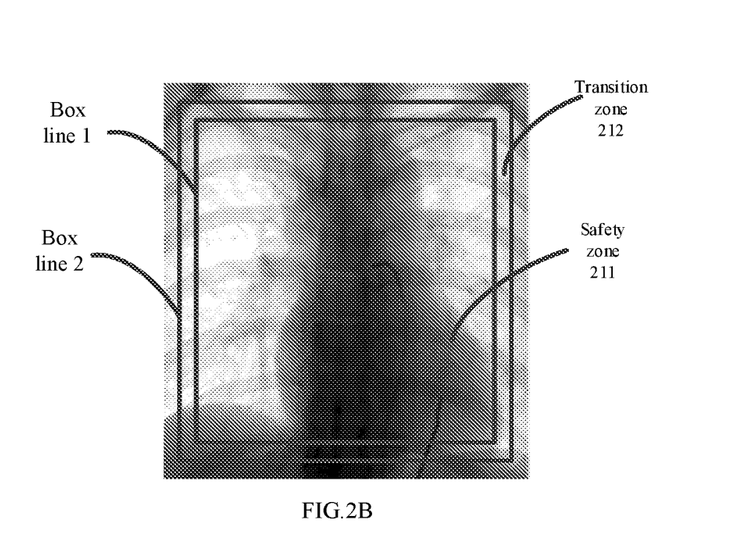
FIG. 2B is a schematic diagram illustrating dividing collection areas of an X-ray detector according to an example of the present disclosure.

The X-ray detector has a collection area in which the X-ray detector can detect X-rays and collect an image. In some examples, the collection area may be pre-divided into a safety zone and a transition zone according to distances of the boards of the zones from edges of the collection area. FIG. 2B is a schematic diagram illustrating dividing a collection area of an X-ray detector according to an example of the present disclosure. A zone enclosed by a box line 1 in FIG. 2B is defined as a safety zone 211. When the contrast medium flows within the safety zone 211, it indicates that the X-ray detector may collect a complete contrast image. A zone between the box line 1 and a box line 2 in FIG. 2B is defined as a transition zone 212. When the contrast medium flows into the transition zone 212, it indicates that the contrast medium is about to flow out of the collection area of the X-ray detector and it is desired to start adjusting the position of the X-ray detector.

Figure 2C:
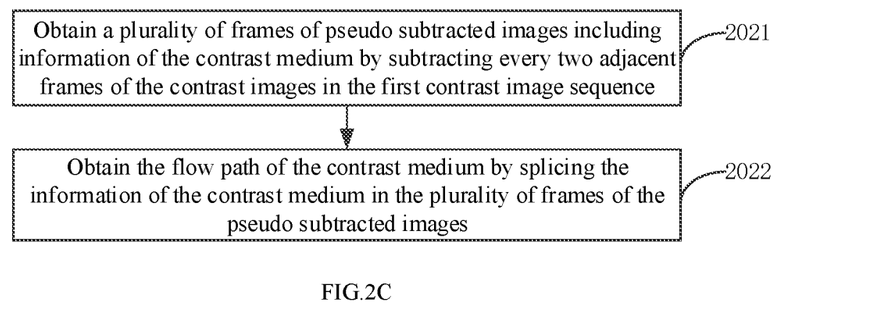
FIG. 2C is a flowchart illustrating a process of obtaining a flow path of a contrast medium according to an example of the present disclosure.
Figure 2D:
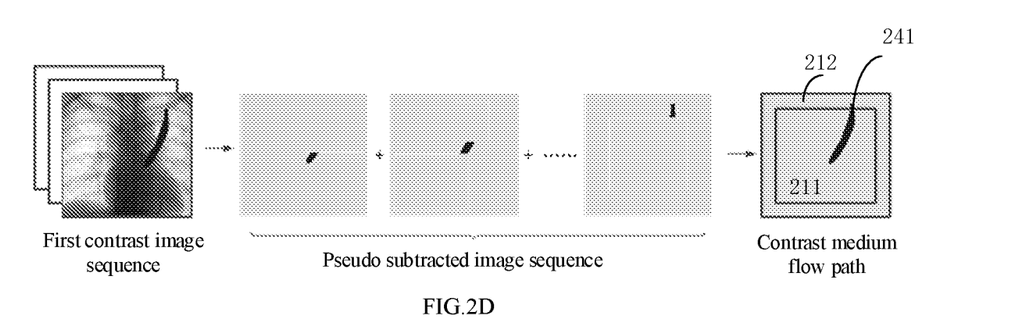
FIG. 2D is a schematic diagram illustrating obtaining a flow path of a contrast medium according to an example of the present disclosure.
Figure 2E:
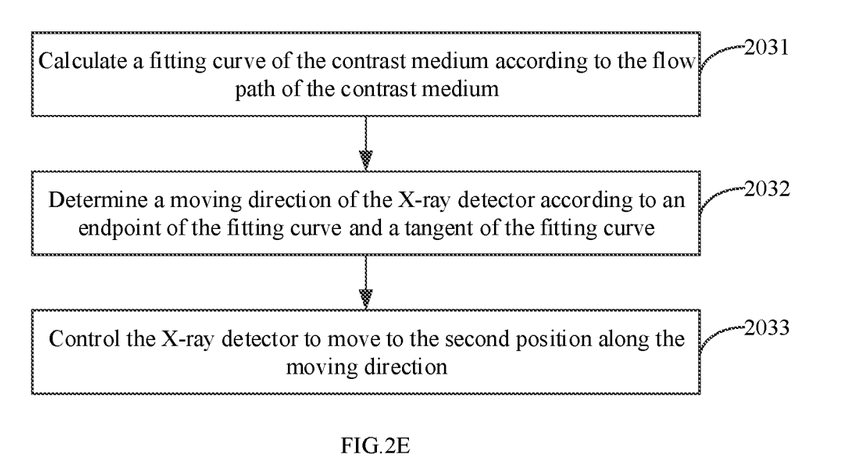
FIG. 2E is a flowchart illustrating a process of controlling an X-ray detector to move from a first position to a second position according to an example of the present disclosure.
Figure 2F:
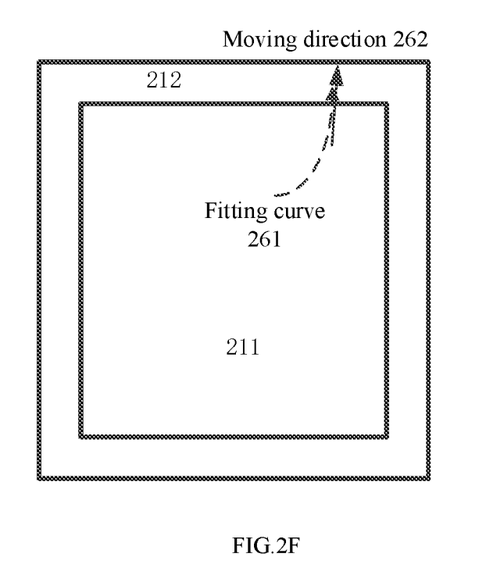
FIG. 2F is a schematic diagram illustrating a fitting curve of a contrast medium obtained by a fitting operation according to an example of the present disclosure.
Figure 2G:
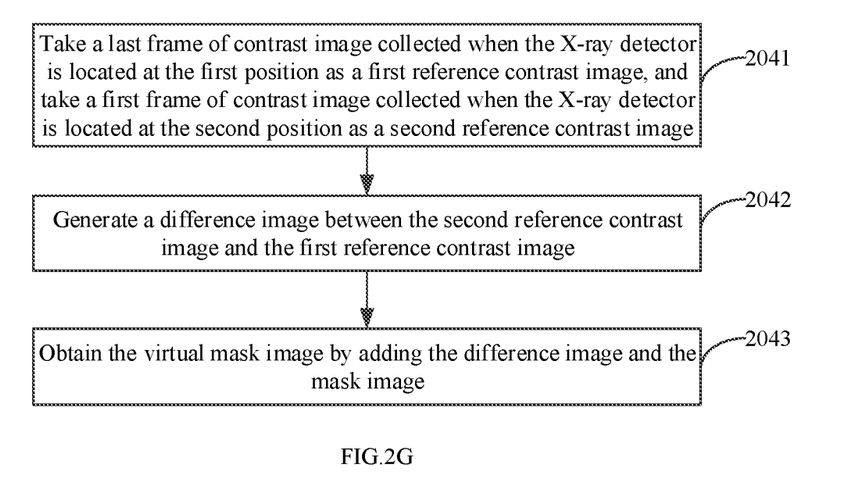
FIG. 2G is a flowchart illustrating a process of obtaining a virtual mask image according to an example of the present disclosure.
Figure 2H:
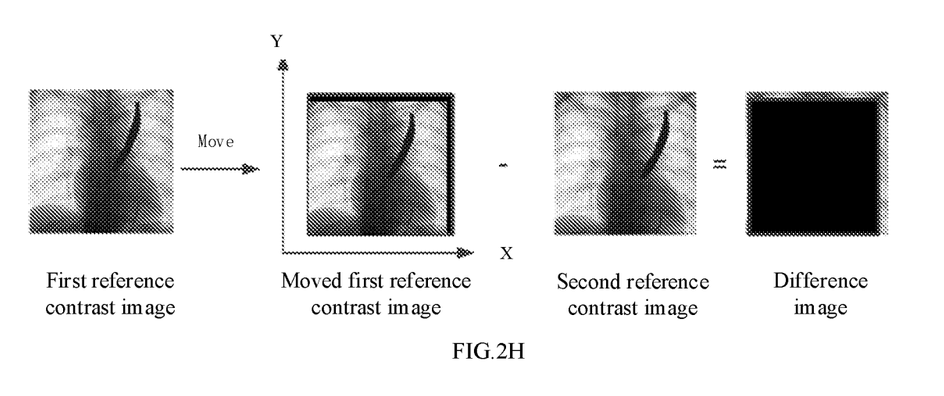
FIG. 2H is a schematic diagram illustrating generating a difference image according to an example of the present disclosure.
Figure 2I:
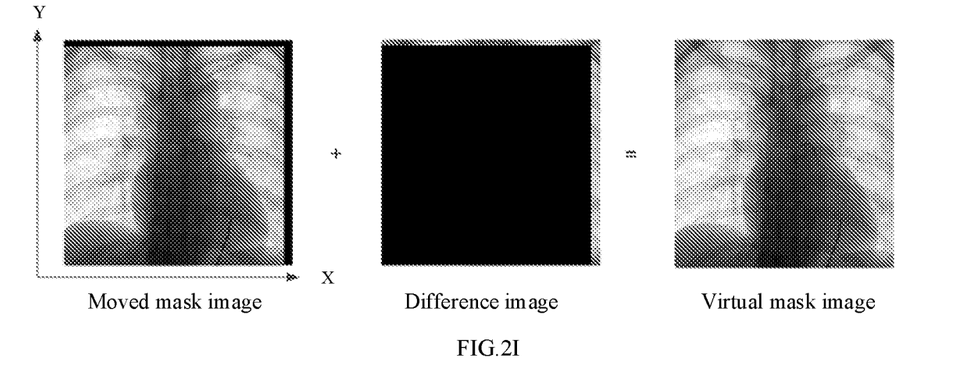
FIG. 2I is a schematic diagram illustrating generating a virtual mask image according to an example of the present disclosure.
Figure 2J:
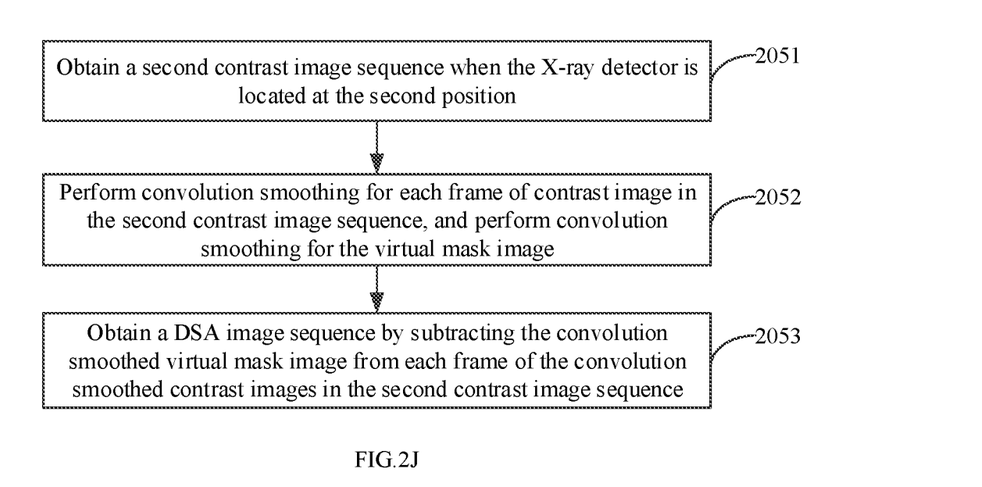
FIG. 2J is a flowchart illustrating a process of generating a DSA image sequence by using a virtual mask image according to an example of the present disclosure.
Figure 2K:
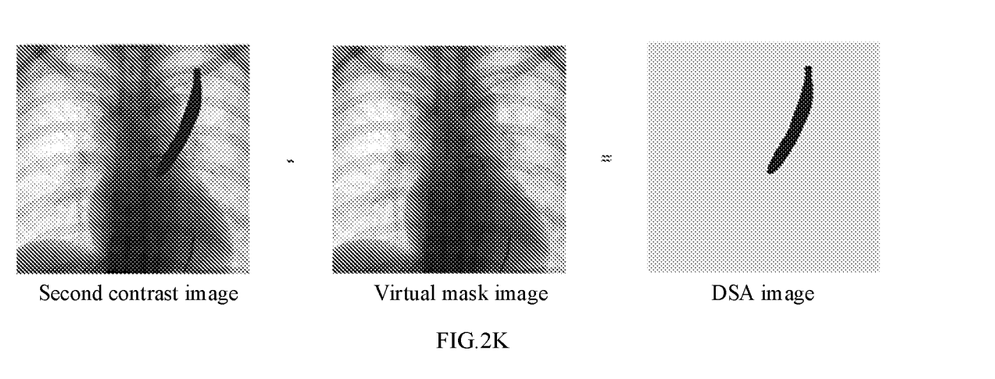
FIG. 2K is a schematic diagram illustrating obtaining a DSA image after movement of an X-ray detector according to an example of the present disclosure.
Figure 2L:
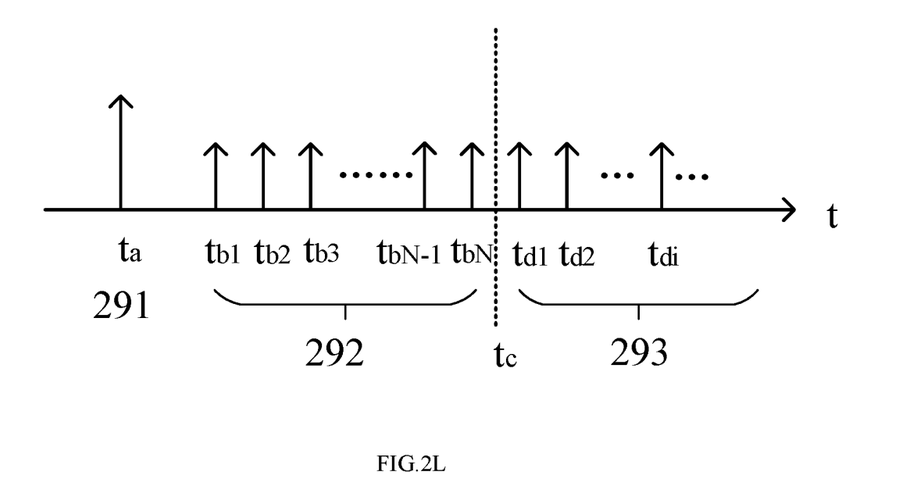
FIG. 2L is a schematic diagram illustrating a timing sequence of capturing a mask image and contrast images according to an example of the present disclosure.

As shown in FIG. 2L, when the X-ray detector is located at the first position, the X-ray detector collects a mask image 291 at a time point $t_a$. In an example, the contrast medium may be injected before the time point $t_a$, and the contrast medium does not reach the detected region at the time point $t_a$. In another example, the contrast medium may be injected between the time point $t_a$ and a time point $t_{b1}$. Then, the X-ray detector may collect a plurality of frames of contrast images in the first contrast image sequence 292 at time points $t_{b1}$-$t_{bN}$ respectively. A time interval between the time point $t_{b1}$ and a time point $t_{b2}$ is the preset time interval. In addition, the contrast medium already reaches the detected region before the time point $t_{b1}$.

At step 202, a flow path of the contrast medium is obtained by analyzing the first contrast image sequence.

The X-ray detector collects contrast images in the first contrast image sequence in real time when being located at the first position. At this step, the flow path of the contrast medium may be obtained by analyzing a series of two adjacent frames of the contrast images. In an example, as shown in FIG. 2C, the flow path of the contrast medium may be obtained through the following steps.

At step 2021, a plurality of frames of pseudo subtracted images including information of contrast medium are obtained by subtracting every two adjacent frames of contrast images in the first contrast image sequence.

At this step, it is assumed that the first contrast image sequence may include N frames of contrast images, which are contrast image 1, contrast image 2, ..., contrast image N-1, and contrast image N, respectively. As shown in FIG. 2L, the contrast image 1 is collected at a time point $t_{b1}$, the contrast image 2 is collected at a time point $t_{b2}$, ..., and the contrast image N is collected at a time point $t_{bN}$.

The following processing may be performed for every two adjacent frames of the contrast images in the first contrast image sequence, such as the contrast image 1 and the contrast image 2, the contrast image 2 and the contrast image 3, ..., and the contrast image N-1 and the contrast image N.

Convolution smoothing processing is performed for the contrast image 1 and the contrast image 2, respectively. In an example, a 5*5 convolution kernel may be selected. An initial subtracted image may be obtained by subtracting the convolution smoothed contrast image 1 from the convolution smoothed contrast image 2. Since the contrast image 2 and the contrast image 1 are contrast images captured by the X-ray detector in the first position with different time points, background parts such as bones and muscles in the two contrast images are the same, and different parts are blood vessel information generated with different time points when the contrast medium flows through the blood vessel. The same background parts in the two frames of the contrast images may be removed by subtraction, and the obtained initial subtracted image may include information reflecting the contrast medium. Further, to remove noises in the initial subtracted image and obtain a pseudo subtracted image including only the information of the contrast medium, a pixel value of each pixel in the initial subtracted image may be compared with a preset pixel threshold. If a pixel with a pixel value is lower than the preset pixel threshold, the pixel is determined as a pixel of the pseudo subtracted image. In an example, the pixel threshold may be set to −50.

Through the above processing, the pseudo subtracted image associated with the contrast image 1 and the contrast image 2 may be obtained, and a pseudo subtracted image sequence may be obtained by processing every two adjacent frames of the contrast images respectively, where each pseudo subtracted image in the pseudo subtracted image sequence includes a portion of contrast medium information. It is to be noted that the above subtraction processing is a real-time processing since the X-ray detector collects contrast images in real time. That is, after the contrast image 1 is obtained in the first contrast image sequence, a pseudo subtracted image may be obtained by calculation every time one new frame of contrast image is collected. That is, a pseudo subtracted image associated with the contrast image 1 and the contrast image 2 may be obtained by calculation between the time point $t_{b2}$ and the time point $t_{b3}$; a pseudo subtracted image associated with the contrast image 2 and the contrast image 3 may be obtained by calculation between the time point $t_{b3}$ and the time point $t_{b4}$, and so on.

At step 2022, the flow path of the contrast medium is obtained by splicing the information of the contrast medium in a plurality of frames of the pseudo subtracted images.

After the pseudo subtracted image sequence is obtained at step 2021, the flow path of the contrast medium within the subject may be constructed by splicing the information of the contrast medium in each frame of the pseudo subtracted images according to a chronological order. FIG. 2D is a schematic diagram illustrating a flow path of a contrast medium obtained after performing steps 2021-2022 according to an example of the present disclosure. After at least two frames of pseudo subtraction images obtained at step 2021, it begins to splice the information of the contrast medium according to the at least two frames of the pseudo subtracted images. Each time a new frame of pseudo subtracted image is obtained at step 2021, a new flow path of the contrast medium is calculated at step 2022. In this way, the flow path of the contrast medium may be reflected in time.

At step 203, when it is determined that the contrast medium is about to flow out of a collection area of the X-ray detector according to the flow path, the X-ray detector is controlled to move to a second position, so that the contrast medium remains within the collection area of the X-ray detector.

In an example, the collection area of the X-ray detector may be pre-divided into a safety zone and a transition zone. Therefore, when it is determined that the contrast medium flows into the transition zone from the safety zone according to the flow path, the X-ray detector may be controlled to move to the second position, so that the contrast medium may be allowed to re-enter the safety zone, thereby ensuring that the contrast medium is always within the collection area of the X-ray detector.

As shown in FIG. 2D, when it is determined that the contrast medium currently already flows into the transition zone 212 from the safety zone 211 according to the flow path 241 of the contrast medium, it indicates that the position of the X-ray detector needs to be adjusted at this time.

In an example, as shown in FIG. 2L, after a contrast image N−1 is obtained at a time point $t_{bN-1}$, a flow path of the contrast medium is calculated based on a previous flow path, the contrast image N−2, and the contrast image N−1. It is determined that the contrast medium is still within the safety zone according to the flow path of the contrast medium. Therefore, there is no need to move the X-ray detector. Then, after a contrast image N is obtained at a time point $t_{bN}$, a new flow path of the contrast medium is calculated based on the flow path, the contrast image N−1, and the contrast image N. It is determined that the contrast medium flows into the transition zone from the safety zone according to the new flow path of the contrast medium. Therefore, it is necessary to move the X-ray detector from the first position to the second position after the time point $t_{bN}$, such as a time point $t_c$.

In an example, as shown in FIG. 2E, the X-ray detector may be controlled to move from the first position to the second position through the following steps.

At step 2031, a fitting curve of the contrast medium is calculated according to the flow path of the contrast medium.

At this step, after it is determined that the contrast medium enters the transition zone from the safety zone, the fitting curve of the contrast medium may be calculated according to the flow path of the contrast medium. For example, the fitting curve of the contrast medium may be obtained by sampling a plurality of pixels from the flow path of the contrast medium, and performing fitting operation for the sampled pixels by a fitting algorithm such as the method of least squares. FIG. 2F is a schematic diagram illustrating a fitting curve 261 of the contrast medium obtained by performing fitting operation for the flow path 241 in FIG. 2D.

At step 2032, a moving direction of the X-ray detector is determined according to a tangent of the fitting curve and an endpoint of the fitting curve.

At this step, as shown in FIG. 2F, the endpoint of the fitting curve and the tangent at the endpoint of fitting curve may be determined after the fitting curve 261 is generated. The direction in which the tangent is pointed is taken as the moving direction 262 of the X-ray detector, as shown in FIG. 2F.

At step 2033, the X-ray detector is controlled to move to the second position along the moving direction.

At this step, after the moving direction of the X-ray detector is determined, the X-ray detector may be controlled to move along the moving direction to ensure that the contrast medium re-enters the safety zone. In an actual moving process, a moving distance of the X-ray detector may be a flow distance of the contrast medium in at least two frames of contrast images collected at the first position, or may be a preset moving distance, which is not limited herein.

At step 204, when the X-ray detector is located at the second position, a virtual mask image is obtained.

After the X-ray detector moves to the second position, a collected image is still a contrast image of the subject since the contrast medium still exists in the subject. To finally obtain a DSA image, it is necessary to obtain a corresponding mask image when the X-ray detector is located at the second position, which is referred to as a virtual mask image in this example. In an example, as shown in FIG. 2G, the virtual mask image may be obtained through the following steps.

At step 2041, a last frame of contrast image collected when the X-ray detector is located at the first position is taken as a first reference contrast image, and a first frame of contrast image collected when the X-ray detector is located at the second position is taken as a second reference contrast image.

When the X-ray detector is located at the first position, a mask image collected before the contrast medium reaches the detected region of the subject. Before the X-ray detector moves from the first position to the second position, the last frame of contrast image collected at the first position is referred to the first reference contrast image. After the X-ray detector moves from the first position to the second position, the first frame of contrast image collected at the second position is referred to the second reference contrast image.

As shown in FIG. 2L, the mask image is an image collected at a time point $t_a$, the first reference contrast image is an image collected at a time point $t_{bN}$, and the second reference contrast image is an image collected at a time point $t_{d1}$.

At step 2042, a difference image between the second reference contrast image and the first reference contrast image is generated.

At this step, pixel values of the first reference contrast image may be compared with pixel values of the second reference contrast image along the moving direction in which the X-ray detector moves from the first position to the second position. Then offset values which reflect the first reference contrast image relative to the second reference contrast image may be determined in two-dimensional directions. The first reference contrast image is moved according to the offset values, as discussed with details below and illustrated in FIG. 2H. Finally, the difference image may be obtained by subtracting the second reference contrast image from the moved first reference contrast image.

To remove noises that may exist in an image, a first smoothed contrast image and a second smoothed contrast image may be obtained by performing convolution smoothing for the first reference contrast image and the second reference contrast image, respectively. For example, a 5*5 convolution kernel may be selected. Pixel values of the first smoothed contrast image may be compared with pixel values of the second smoothed contrast image along the moving direction 262 as shown in FIG. 2F. According to a comparison result, when pixel value differences in any row satisfy a successful condition in a Y direction and/or pixel value differences in any column satisfy the successful condition in a X direction, it may be determined that the row and/or column are taken as image edges of the first smoothed contrast image in the second smoothed contrast image. In an example, the successful condition may be that a ratio exceeds a preset successful coefficient F, where the ratio is obtained by dividing the number of pixels whose pixel difference value is smaller than N by the number of pixels in a row or in a column, N may be set to 10, and the successful coefficient F may be set to 90%.

Specifically, pixels of the first smoothed contrast image edges are firstly obtained according to the moving direction 262 as shown in FIG. 2F. For example, the edge in the Y direction of the first smoothed contrast image may be the topmost row of the image, and the edge in the X direction may be the rightmost column of the image. Then, taking the Y direction as an example, each row of the upper side of the second smoothed contrast image is sequentially subtracted from the edge of the first smoothed contrast image according to the moving direction 262 shown in FIG. 2F. Until the pixel value differences obtained by subtraction satisfy the successful condition, it may be considered that the row is taken as the edge of the first smoothed contrast image in the second smoothed contrast image. That is, the first row (topmost row) of the second smoothed contrast image is subtracted from the edge (topmost row) of the first smoothed contrast image. If the result does not satisfy the successful condition, the second row of the second smoothed contrast image is subtracted from the edge of the first smoothed contrast image. If the result still does not satisfy the successful condition, the third row of the second smoothed contrast image is subtracted from the edge of the first smoothed contrast image. If the result satisfies the successful condition, the third row is taken as the edge of the first smoothed contrast image in the second smoothed contrast image. Same processing is performed for the X direction.

Next, the offset values in the X direction and the Y direction which reflecting the first reference contrast image relative to the second reference contrast image may be determined according to distances between the edges of the first smoothed contrast image in the second smoothed contrast image and the edges of the second smoothed contrast image. Still taking the above description as an example, for the Y direction, the edge of the first smooth contrast image in the second smooth contrast image is the third row and the edge of the second smooth contrast image is the first row, so the offset value is 3−1=2. FIG. 2H is a schematic diagram illustrating generating a difference image according to an example of the present disclosure. As shown in FIG. 2H, if the offset value in the X direction is x and the offset value in the Y direction is y, the first reference contrast image may be moved by x pixels in the X direction and y pixels in the Y direction, respectively. Then, the difference image between the first reference contrast image and the second reference contrast image may be obtained by subtracting the second reference contrast image from the moved first reference contrast image.

At step 2043, a virtual mask image is obtained by adding the difference image and the mask image.

After the X-ray detector moves to the second position, the mask image originally captured at the first position cannot be directly used to generate a DSA image at the new position. However, since the moving distance of the X-ray detector is relatively small, comparing with the mask image, the change of the virtual mask image corresponding to the second position can lie in the increase of the image edges.

FIG. 2I is a schematic diagram illustrating generating a virtual mask image according to an example of the present disclosure. In an example, a moved mask image is obtained by moving the mask image by x pixels in the X direction and y pixels in the Y direction, where x and y are the offset values obtained at step 2042. As described in step 2042, the offset values in the direction X and the direction Y are determined according to the first reference contrast image and the second reference contrast image. Then, a virtual mask image corresponding to the second position may be obtained by adding the moved mask image and the difference image.

At step 205, a DSA image sequence is generated by using the virtual mask image.

After the X-ray detector moves to the second position, the virtual mask image is generated at step 204. In an example, as shown in FIG. 2J, the angiography may be completed by generating the DSA image sequence with the virtual mask image through the following steps.

At step 2051, a second contrast image sequence is obtained when the X-ray detector is located at the second position.

At this step, same as at the first position, the X-ray detector may continue to collect a contrast image sequence according to a preset time interval after moving to the second position. To distinguish from the first contrast image sequence collected at the first position, when the X-ray detector is located at the second position the collected contrast image sequence is referred to a second contrast image sequence.

As shown in FIG. 2L, after the X-ray detector is moved to the second position at a time point $t_c$, the second contrast image sequence 293 is obtained by collecting a plurality of frames of contrast images at time points $t_{d1}, t_{d2}, \ldots, t_{di}$, and the like respectively. The second contrast image sequence 293 includes at least one frame of contrast image.

At step 2052, convolution smoothing is performed for each frame of the contrast image in the second contrast image sequence, and convolution smoothing is performed for the virtual mask image.

Same as the description of convolution smoothing in the above steps, in an example, the convolution smoothing may still be performed for contrast images in the second contrast image sequence and the virtual mask image by using the 5*5 convolution kernel.

At step 2053, a DSA image sequence is obtained by subtracting the convolution smoothed virtual mask image from each frame of the convolution smoothed contrast images in the second contrast image sequence.

FIG. 2K is a schematic diagram illustrating obtaining a DSA image after movement of an X-ray detector according to an example of the present disclosure. A contrast image in the second contrast image sequence may be referred to a second contrast image. A DSA image may be obtained by subtracting the convolution smoothed virtual mask image from a convolution smoothed second smoothed contrast image. When the X-ray detector is located at the second position, a DSA image sequence may be obtained by performing the above operation for each frame of the second contrast image in the second contrast image sequence subjected to convolution smooth.

In an example, when the X-ray detector is located at the first position, a DSA image is obtained by subtracting the mask image from a contrast image in the first contrast image sequence. This method may use a conventional DSA technology and will not described herein.

It may be seen from the above examples that a collection area of a X-ray detector is pre-divided into a safety zone and a transition zone, and thus, when it is determined that a contrast medium flows into the transition zone from the safety zone by analyzing a flow path of the contrast medium in real time, the X-ray detector may be controlled to move. In this way, the contrast medium is always within the safety zone by automatically controlling the X-ray detector to move. After movement of the X-ray detector, a virtual mask image may be obtained by calculation, thereby generating a DSA image sequence at the new position with the virtual mask image. No manual operation is required in the entire angiography process, so that the implementation is convenient and the angiographic efficiency may be improved.

Corresponding to the above examples of the angiography system and the angiography method, the present disclosure also provides examples of an angiography apparatus and an image processing device.

Figure 3:
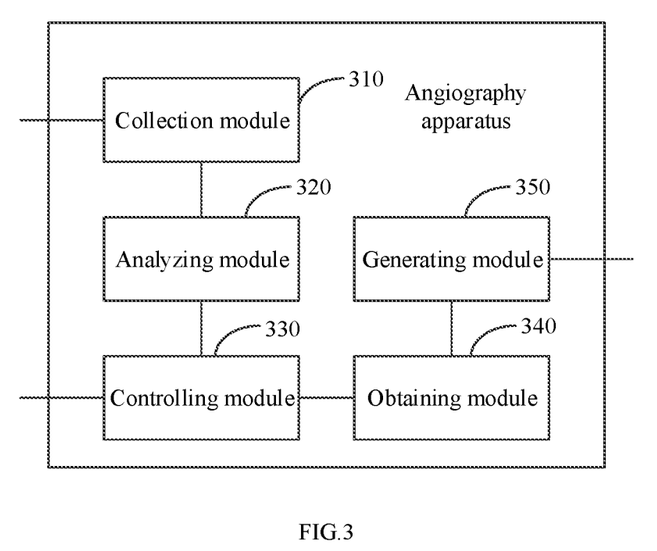
FIG. 3 is a schematic diagram illustrating an angiography apparatus according to an example of the present disclosure.

FIG. 3 is a block diagram illustrating an angiography apparatus according to an example of the present disclosure. The apparatus may be applied to a DSA system including an X-ray detector, and includes a collecting module 310, an analyzing module 320, a controlling module 330, an obtaining module 340 and a generating module 350.

The collecting module 310 is configured to obtain contrast images and a mask image. When the X-ray detector is located at a first position, the collecting module 310 obtains a first contrast image sequence including a plurality of frames of contrast images collected by the X-ray detector.

The analyzing module 320 is configured to obtain a flow path of a contrast medium by analyzing the first contrast image sequence.

The controlling module 330 is configured to, when it is determined that the contrast medium is about to flow out of a collection area of the X-ray detector according to the flow path, control the X-ray detector to move to a second position, so that the contrast medium remains within the collection area of the X-ray detector.

The obtaining module 340 is configured to, when the X-ray detector is located at the second position, obtain a virtual mask image based on a mask image collected when the X-ray detector is located at the first position, the last frame of contrast image collected when the X-ray detector is located at the first position and the first frame of contrast image of a second contrast image sequence collected when the X-ray detector is located at the second position.

The generating module 350 is configured to generate a DSA image sequence by using the virtual mask image and the second contrast image sequence.

Figure 4:
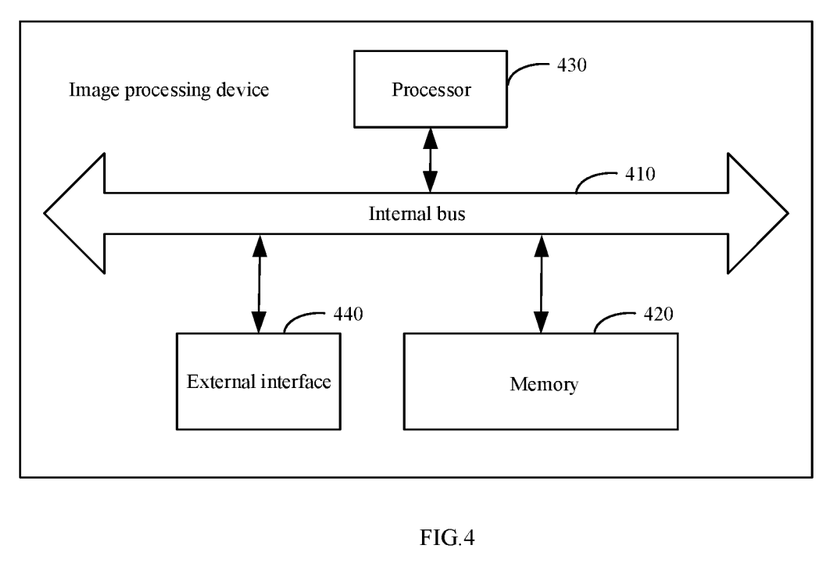
FIG. 4 is a schematic diagram illustrating an image processing device according to an example of the present disclosure.

FIG. 4 is a schematic diagram illustrating an image processing device according to an example of the present disclosure. The image processing device may be applied to a DSA system including an X-ray detector, and includes an internal bus 410, and a memory 420, a processor 430 and an external interface 440 which are connected via the internal bus 410.

The external interface 440 is configured to connect the X-ray detector.

The memory 420 is configured to store machine readable instructions corresponding to a control logic for angiography.

The processor 430 is configured to read the machine readable instructions in the memory and execute the instructions to implement the following operations of: obtaining a first contrast image sequence comprising a plurality of frames of contrast images collected by the X-ray detector at a first position; obtaining a flow path of a contrast medium by analyzing the first contrast image sequence; when it is determined that the contrast medium is about to flow out of a collection area of the X-ray detector according to the flow path, controlling the X-ray detector to move to a second position, so that the contrast medium remains within the collection area of the X-ray detector; when the X-ray detector is located at the second position, obtaining a virtual mask image based on a mask image collected when the X-ray detector is located at the first position, the last frame of contrast image collected when the X-ray detector is located at the first position and the first frame of contrast image collected when the X-ray detector is located at the second position; and generating a DSA image by using the virtual mask image.

In an example, obtaining the flow path of the contrast medium by analyzing the first contrast image sequence includes: obtaining a plurality of frames of pseudo subtracted images comprising information of the contrast medium by subtracting every two adjacent frames of the contrast images in the first contrast image sequence; and obtaining the flow path of the contrast medium by splicing the information of the contrast medium in the plurality of frames of the pseudo subtracted images.

Further, obtaining the plurality of frames of the pseudo subtracted images comprising the information of the contrast medium by subtracting every two adjacent frames of the contrast images in the first contrast image sequence includes: for the every two adjacent frames of the contrast images: performing convolution smoothing for the two frames of the contrast images respectively; obtaining an initial subtracted image by performing subtraction for the frames of the two convolution smoothed contrast images; and determining a pixel in the initial subtracted image having a pixel value lower than a preset pixel threshold as a pixel of a pseudo subtracted image.

In an example, the collection area of the X-ray detector comprises a safety zone and a transition zone.

Further, when it is determined that the contrast medium is about to flow out of the collection area of the X-ray detector according to the flow path, controlling the X-ray detector to move to the second position so that the contrast medium remains within the collection area of the X-ray detector includes: when it is determined that the contrast medium is about to flow into the transition zone from the safety zone according to the flow path, controlling the X-ray detector to move to the second position so that the contrast medium re-enters the safety zone.

In an example, controlling the X-ray detector to move to the second position includes: calculating a fitting curve of the contrast medium according to the flow path of the contrast medium; determining a moving direction of the X-ray detector according to an endpoint of the fitting curve and a tangent of the fitting curve; and controlling the X-ray detector to move to the second position along the moving direction.

In an example, obtaining the virtual mask image when the X-ray detector is located at the second position includes: taking a last frame of contrast image collected when the X-ray detector is located at the first position as a first reference contrast image; taking a first frame of contrast image collected when the X-ray detector is located at the second position as a second reference contrast image; generating a difference image between the second reference contrast image and the first reference contrast image; and obtaining the virtual mask image by adding the difference image and the mask image.

Further, generating the difference image between the second reference contrast image and the first reference contrast image includes: comparing pixel values of the first reference contrast image with pixel values of the second reference contrast image along the moving direction in which the X-ray detector moves from the first position to the second position; determining offset values which reflecting the first reference contrast image relative to the second reference contrast image in a two-dimensional direction according to a comparison result; moving the first reference contrast image according to the offset values; and obtaining the difference image by subtracting the second reference contrast image from the moved first reference contrast image.

Further, obtaining the virtual mask image by adding the difference image and the mask image includes: moving the mask image according to the offset values; and obtaining the virtual mask image by adding the moved mask image and the difference image.

In an example, generating the DSA image sequence by using the virtual mask image includes:
obtaining a second contrast image sequence when the X-ray detector is located at the second position; performing convolution smoothing for the virtual mask image; and for each frame of contrast image in the second contrast image sequence: performing convolution smoothing for the contrast image; and obtaining the DSA image by subtracting the convolution smoothed virtual mask image from the convolution smoothed contrast images.

In addition, the angiography process in an example of the present disclosure may also be included in a non-volatile computer readable storage medium. The storage medium may be connected with a processing device for executing instructions and stores machine readable instructions corresponding to a control logic for angiography. These instructions can be executed by the processing device, and the above machine readable instructions are configured to implement the following operations of: obtaining a first contrast image sequence comprising a plurality of frames of contrast images collected by the X-ray detector at a first position; obtaining a flow path of a contrast medium by analyzing the first contrast image sequence; when it is determined that the contrast medium is about to flow out of a collection area of the X-ray detector according to the flow path, controlling the X-ray detector to move to a second position, so that the contrast medium remains within the collection area of the X-ray detector; when the X-ray detector is located at the second position, obtaining a virtual mask image based on a mask image collected when the X-ray detector is located at the first position, the last frame of contrast image collected when the X-ray detector is located at the first position and the first frame of contrast image collected when the X-ray detector is located at the second position; and generating a DSA image by using the virtual mask image.

In an example of the present disclosure, a computer readable storage medium may be applied in different forms. For example, the machine readable storage medium in different examples may be: a Random Access Memory (RAM), a volatile memory, a non-volatile memory, a flash memory, a storage drive (e.g. hard disk drive), a solid state hard disk, any type of storage disk (e.g., compact disk, Digital Video Disk (DVD)), or a similar storage medium, or a combination thereof.

For simplicity and illustrative purposes, the present disclosure is described by referring mainly to examples thereof. In the above descriptions, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

The above description is merely preferred examples of the present disclosure and is not intended to limit the present disclosure in any form. Although the present disclosure is disclosed by the above examples, the examples are not intended to limit the present disclosure. Those skilled in the art, without departing from the scope of the technical scheme of the present disclosure, may make a plurality of changes and modifications of the technical scheme of the present disclosure by the method and technical content disclosed above.

Therefore, without departing from the scope of the technical scheme of the present disclosure, based on technical essences of the present disclosure, any simple alterations, equal changes and modifications should fall within the protection scope of the technical scheme of the present disclosure. Accordingly, other embodiments are within the scope of the following claims.

What is claimed is:

1. An angiography method for a Digital Subtraction Angiography (DSA) system comprising an X-ray detector, the method comprising:
   obtaining a first contrast image sequence comprising a plurality of frames of contrast images collected by the X-ray detector at a first position after a contrast medium flows into a collection area of the X-ray detector;
   generating a flow path of the contrast medium by analyzing the first contrast image sequence;
   in response to determining that the contrast medium is about to flow out of the collection area of the X-ray detector according to the flow path, controlling the X-ray detector to move to a second position, so that the contrast medium remains within the collection area of the X-ray detector; and
   when the X-ray detector is located at the second position, generating a virtual mask image based on a mask image collected when the X-ray detector is located at the first position and before the contrast medium flows into the collection area, a last frame of contrast image collected when the X-ray detector is located at the first position and a first frame of contrast image collected when the X-ray detector is located at the second position.

2. The method of claim 1, wherein generating the flow path of the contrast medium comprises:
   obtaining a plurality of frames of pseudo subtracted images comprising information of the contrast medium by subtracting every two adjacent frames of the plurality of frames of contrast images in the first contrast image sequence; and
   generating the flow path of the contrast medium by splicing the information of the contrast medium in the plurality of frames of pseudo subtracted images.

3. The method of claim 2, wherein obtaining the plurality of frames of pseudo subtracted images comprises:
   for every two adjacent frames of the plurality of frames of contrast images:
      performing respective convolution smoothing for each of the two adjacent frames of the plurality of frames of contrast images;
      generating an initial subtracted image by performing subtraction for the two adjacent convolution smoothed frames of contrast images; and
      determining a pixel in the initial subtracted image having a pixel value lower than a preset pixel threshold to be a pixel of a pseudo subtracted image for the two adjacent frames of the plurality of frames of contrast images.

4. The method of claim 1, wherein the collection area of the X-ray detector comprises a safety zone and a transition zone.

5. The method of claim 4, wherein controlling the X-ray detector to move to the second position comprises:
   in response to determining that the contrast medium is about to flow from the safety zone into the transition zone according to the flow path, controlling the X-ray detector to move to the second position so that the contrast medium re-enters the safety zone of the collection area of the X-ray detector.

6. The method of claim 5, wherein a moving distance of the X-ray detector from the first position to the second position is determined based on a flow distance of the contrast medium in at least two frames of contrast images collected by the X-ray detector at the first position or at a present position, such that the contrast medium is kept within the collection area of the X-ray detector.

7. The method of claim 1, wherein controlling the X-ray detector to move to the second position comprises:
   calculating a fitting curve of the contrast medium according to the flow path of the contrast medium;
   determining a moving direction of the X-ray detector according to an endpoint of the fitting curve and a tangent of the fitting curve; and
   controlling the X-ray detector to move to the second position along the moving direction.

8. The method of claim 1, wherein obtaining the virtual mask image when the X-ray detector is located at the second position comprises:
   taking the last frame of contrast image collected when the X-ray detector is located at the first position as a first reference contrast image;
   taking the first frame of contrast image collected when the X-ray detector is located at the second position as a second reference contrast image;
   generating a difference image between the second reference contrast image and the first reference contrast image; and
   obtaining the virtual mask image by adding the difference image and the mask image.

9. The method of claim 8, wherein generating the difference image between the second reference contrast image and the first reference contrast image comprises:
   determining offset values that reflect the first reference contrast image relative to the second reference contrast image;
   moving the first reference contrast image according to the offset values; and
   generating the difference image by subtracting the second reference contrast image from the moved first reference contrast image.

10. The method of claim 9, wherein determining the offset values comprises:
   comparing pixel values of the first reference contrast image with pixel values of the second reference contrast image along the moving direction in which the X-ray detector moves from the first position to the second position; and
   determining the offset values in a two-dimensional direction according to a result of the comparison.

11. The method of claim 9, wherein determining the offset values comprises:
   generating a first smoothed contrast image and a second smoothed contrast image by performing convolution smoothing for the first reference contrast image and the second reference contrast image, respectively;
   comparing pixel values of the first smoothed contrast image with pixel values of the second smoothed contrast image along the moving direction;
   determining edges of the first smoothed contrast image in the second smoothed contrast image according to a result of the comparison; and
   determining the offset values in a two-dimensional direction according to distance between the edges of the first smoothed contrast image in the second smoothed contrast image and edges of the second smoothed contrast image.

12. The method of claim 9, wherein obtaining the virtual mask image by adding the difference image and the mask image comprises:
   moving the mask image according to the offset values; and
   obtaining the virtual mask image by adding the moved mask image and the difference image.

13. The method of claim 1, further comprising obtaining a DSA image sequence by
   obtaining a second contrast image sequence comprising a plurality of frames of second contrast images collected by the X-ray detector at the second position,
   performing convolution smoothing for the virtual mask image, and
   for each frame of second contrast image in the second contrast image sequence:
      performing convolution smoothing for the frame of second contrast image, and
      generating a respective DSA image by subtracting the convolution smoothed virtual mask image from the convolution smoothed frame of second contrast image,
      wherein the DSA image sequence comprises the respective DSA images for the frames of second contrast images in the second contrast image sequence.

14. The method of claim 13, wherein obtaining the DSA image sequence further comprises:
   generating respective first DSA images by using the mask image and the frames of contrast images in the first contrast image sequence,
   wherein the DSA image sequence comprises the respective first DSA images for the frames of contrast images in the first contrast image sequence.

15. A Digital Subtraction Angiography (DSA) system comprising:
   a DSA main device comprising:
      an examination bed,
      a fixed gantry,
      a rotatable mechanical arm arranged on the fixed gantry, and
      an X-ray emitter and an X-ray detector which are mounted on two ends of the mechanical arm, the X-ray detector being configured to collect contrast images and a mask image; and
   an image processing device configured to:
      obtain a first contrast image sequence comprising a plurality of frames of contrast images collected by the X-ray detector at a first position after a contrast medium flows into a collection area of the X-ray detector;
      generate a flow path of the contrast medium by analyzing the first contrast image sequence;
      in response to determining that the contrast medium is about to flow out of the collection area of the X-ray detector according to the flow path, control the X-ray detector to move to a second position, so that the contrast medium remains within the collection area of the X-ray detector;
      when the X-ray detector is located at the second position, obtain a virtual mask image based on a mask image collected when the X-ray detector is located at the first position, a last frame of contrast image of the first contrast image sequence collected when the X-ray detector is located at the first position and a first frame of contrast image of a second contrast image sequence collected when the X-ray detector is located at the second position; and
      generate a DSA image sequence by using the virtual mask image and the second contrast image sequence.

16. The DSA system of claim 15, wherein the image processing device is configured to generate the flow path of the contrast medium by
   obtaining a plurality of frames of pseudo subtracted images comprising information of the contrast medium by subtracting every two adjacent frames of the plurality of frames of contrast images in the first contrast image sequence; and
   generating the flow path of the contrast medium by splicing the information of the contrast medium in the plurality of frames of pseudo subtracted images.

17. The DSA system of claim 15, wherein the collection area of the X-ray detector comprises a safety zone and a transition zone, and
   wherein the image processing device is configured to control the X-ray detector to move to the second position by controlling the X-ray detector to move to the second position in response to determining that the contrast medium is about to flow from the safety zone into the transition zone according to the flow path so that the contrast medium re-enters the safety zone of the collection area of the X-ray detector.

18. The DSA system of claim 15, wherein the image processing device is configured to obtain the virtual mask image by
   determining offset values that reflect the last frame of contrast image of the first contrast image sequence as a first reference contrast image relative to the first frame of contrast image of the second contrast image sequence as a second reference contrast image,
   moving the first reference contrast image according to the offset values,
   generating a difference image by subtracting the second reference contrast image from the moved first reference contrast image,
   moving the mask image according to the offset values, and
   adding the difference image and the moved mask image to obtain the virtual mask image.

19. The DSA system of claim 15, wherein the image processing device is configured to generate the DSA image sequence by
   performing convolution smoothing for the virtual mask image; and
   for each frame of second contrast image in the second contrast image sequence:
      performing convolution smoothing for the frame of second contrast image; and
      generating a respective DSA image by subtracting the convolution smoothed virtual mask image from the convolution smoothed frame of second contrast image,
      wherein the DSA image sequence comprises the respective DSA images for the frames of second contrast images in the second contrast image sequence.

20. An image processing device of a Digital Subtraction Angiography (DSA) system comprising an X-ray detector, the image processing device comprising:
   at least one processor;
   a memory configured to store machine readable instructions corresponding to a control logic for angiography;

an external interface configured to connect the X-ray detector; and an internal bus through which the memory, the processor, and the external interface are connected, wherein the processor is configured to read the machine readable instructions in the memory and execute the instructions to perform operations comprising:

obtaining a first contrast image sequence comprising a plurality of frames of contrast images collected by the X-ray detector at a first position after a contrast medium flows into a collection area of the X-ray detector;

generating a flow path of the contrast medium by analyzing the first contrast image sequence;

in response to determining that the contrast medium is about to flow out of the collection area of the X-ray detector according to the flow path, controlling the X-ray detector to move to a second position, so that the contrast medium remains within the collection area of the X-ray detector;

when the X-ray detector is located at the second position, obtaining a virtual mask image based on a mask image collected when the X-ray detector is located at the first position, a last frame of contrast image of the first contrast image sequence collected when the X-ray detector is located at the first position and a first frame of contrast image of a second contrast image sequence collected when the X-ray detector is located at the second position; and generating a DSA image sequence by using the virtual mask image and the second contrast image sequence.

* * * * *